US010857395B2

(12) United States Patent
Myers et al.

(10) Patent No.: US 10,857,395 B2
(45) Date of Patent: Dec. 8, 2020

(54) ORAL CARE COMPOSITIONS

(71) Applicant: Colgate-Palmolive Company, New York, NY (US)

(72) Inventors: Carl Myers, Wayne, NJ (US); Rehana Begum-Gafur, Clifton, NJ (US); Katelyn Duchemin, Budd Lake, NJ (US); Melissa Muir, Lopatcong, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/702,618

(22) Filed: Dec. 4, 2019

(65) Prior Publication Data

US 2020/0101329 A1    Apr. 2, 2020

Related U.S. Application Data

(63) Continuation of application No. 16/273,640, filed on Feb. 12, 2019, now Pat. No. 10,525,289, which is a continuation of application No. 15/667,698, filed on Aug. 3, 2017, now Pat. No. 10,238,896.

(60) Provisional application No. 62/373,567, filed on Aug. 11, 2016.

(51) Int. Cl.
| | | |
|---|---|---|
| *A61K 8/21* | (2006.01) | |
| *A61Q 11/00* | (2006.01) | |
| *A61K 8/43* | (2006.01) | |
| *A61K 8/46* | (2006.01) | |
| *A61K 8/24* | (2006.01) | |
| *A61K 8/41* | (2006.01) | |

(52) U.S. Cl.
CPC ............... *A61Q 11/00* (2013.01); *A61K 8/21* (2013.01); *A61K 8/24* (2013.01); *A61K 8/416* (2013.01); *A61K 8/43* (2013.01); *A61K 8/463* (2013.01); *A61K 2800/805* (2013.01)

(58) Field of Classification Search
CPC ...................................................... A61K 8/21
See application file for complete search history.

(56) References Cited

U.S. PATENT DOCUMENTS

| | | |
|---|---|---|
| 3,956,480 A | 5/1976 | Dichter et al. |
| 4,042,679 A | 8/1977 | Gaffar |
| 4,080,441 A | 3/1978 | Gaffar et al. |
| 4,110,429 A | 8/1978 | Gaffar et al. |
| 4,118,472 A | 10/1978 | Gaffar et al. |
| 4,118,474 A | 10/1978 | Gaffar et al. |
| 4,118,475 A | 10/1978 | Gaffar et al. |
| 4,137,303 A | 1/1979 | Gaffar et al. |
| 4,183,916 A | 1/1980 | Rodon |
| 4,188,372 A | 2/1980 | Gaffar |
| 4,224,309 A | 9/1980 | Gaffar et al. |
| 4,273,759 A | 6/1981 | Gaffar et al. |
| 4,323,551 A | 4/1982 | Parran, Jr. |
| 4,339,430 A | 7/1982 | Gaffar |
| 4,370,314 A | 1/1983 | Gaffar |
| 5,158,763 A | 10/1992 | Gaffar et al. |
| 5,681,549 A | 10/1997 | McLaughlin et al. |
| 6,117,417 A | 9/2000 | Wicks et al. |
| 6,471,948 B1 | 10/2002 | Adamy et al. |
| 6,723,305 B2 | 4/2004 | DePierro et al. |
| 8,758,729 B2 | 6/2014 | Nowak et al. |
| 9,241,885 B2 | 1/2016 | Roberge et al. |
| 2005/0180927 A1 | 8/2005 | Aldous et al. |
| 2006/0171907 A1 | 8/2006 | Scott et al. |
| 2013/0224270 A1 | 8/2013 | Robinson et al. |
| 2015/0305993 A1 | 10/2015 | Rege et al. |

FOREIGN PATENT DOCUMENTS

| | | |
|---|---|---|
| EP | 0664694 | 8/1995 |
| WO | 2008/041055 | 4/2008 |

OTHER PUBLICATIONS

International Search Report and Written Opinion of the International Searching Authority in International Application No. PCT/US2017/045214, dated Oct. 13, 2017.

*Primary Examiner* — Benjamin J Packard

(57) ABSTRACT

This application provides, among other things, novel aqueous oral care compositions useful for combining and delivering poorly compatible ingredients, for example to deliver effective levels of cationic antibacterial agents in combination with short chain polyphosphate salts that protect against erosion and staining, by addition of a stabilizing amount of an anionic surfactant and methods for making and using the same.

17 Claims, No Drawings

ORAL CARE COMPOSITIONS

CROSS-REFERENCE TO RELATED APPLICATIONS

This application is a continuation of U.S. application Ser. No. 16/273,640, which is a national application filed under 35 U.S.C. § 111, which is a continuation application claiming priority to and the benefit of U.S. application Ser. No. 15/667,698, filed on Aug. 3, 2017, which claims priority to and the benefit of U.S. provisional application 62/373,567, filed on Aug. 11, 2016, the contents of which are incorporated by reference herein in their entireties.

BACKGROUND

This application relates, inter alia, to novel aqueous oral care compositions useful for combining and delivering poorly compatible ingredients, for example to deliver effective levels of cationic antibacterial agents in combination with polyphosphate salts that protect against erosion and staining.

Biofilms form when bacteria adhere to surfaces in some form of watery environment and begin to excrete a slimy, glue-like substance that can stick to all kinds of materials—metals, plastics, soil particles, medical implant materials, biological tissues. Dental plaque is a biofilm that adheres to tooth and other oral surfaces, particularly at the gingival margin, and is implicated in the occurrence of gingivitis, periodontitis, caries and other forms of periodontal disease. Dental plaque is cohesive and highly resistant to removal from teeth and/or oral surfaces. Bacteria associated with dental plaque convert sugar to glucans, which are insoluble polysaccharides that provide plaque with its cohesive properties. Anaerobic bacteria in plaque metabolize sugar to produce acids which dissolve tooth minerals, damaging the enamel and eventually forming dental caries. Saliva can buffer acids produced by bacteria and promote remineralization of the enamel, but extensive plaque can block the saliva from contact with the enamel. Redeposition of minerals in the biofilm forms a hard deposit on the tooth called calculus (or tartar), which becomes a local irritant for the gums, causing gingivitis.

Various antibacterial agents can retard the growth of bacteria and thus reduce the formation of biofilm on oral surfaces. In many cases, these antibacterial agents are cationic, for example quaternary ammonium surfactants such as cetyl pyridinium chloride (CPC), bisguanides such as chlorhexidine, metal cations such as zinc or stannous ions, and guanidines such as arginine.

Everyday activities such as smoking or other oral use of tobacco products, and eating, chewing or drinking certain foods and beverages (particularly coffee, tea, cola drinks, and red wine), cause undesirable staining of surfaces of teeth. Staining can also result from microbial activity, including that associated with dental plaque. The chromogens or color causing substances in these materials become part of the pellicle layer and can permeate the enamel layer. Even with regular brushing and flossing, years of chromogen accumulation can impart noticeable tooth discoloration.

A tooth is comprised of an inner dentin layer and an outer hard enamel layer that is the protective layer of the tooth. The enamel layer of a tooth is naturally opaque, and white or a slightly off-white color. The enamel layer is composed of hydroxyapatite mineral crystals that create a somewhat porous surface. These hydroxyapatite crystals form microscopic hexagonal rods or prisms that make up the enamel surface. As a result, the surface of the enamel presents microscopic spaces or pores between the prisms. Without limiting the mechanism, function, or utility of the present disclosure, it is believed that this porous nature of the enamel is where discoloring substances permeate the enamel and discolor the teeth.

Since the compounds that stain the teeth are typically anionic materials, cationic antibacterial agents can cause or enhance staining by facilitating the deposit of chromogens or by forming salts with minerals.

One approach to reducing staining and erosion as well as reducing biofilm formation is the use of a dentifrice, such as a mouthwash, containing mineral agents useful in stain removal. Polyphosphate salts, for example, exhibit significant stain fighting ability, and when used in oral care products, they deposit onto and protect the tooth surface, as well as complexing with free calcium, thereby starving bacteria and reducing calculus deposition. However, when phosphates are combined with cationic antibacterial agents, particularly in high water formulations where the two can readily interact in solution, the phosphates and the cationic antibacterial agents can complex to form insoluble precipitates, thereby inactivating both components.

There is thus a need for novel oral compositions and methods that inhibit staining and biofilm formation, and in particular that can provide both the anti-staining and anti-calculus benefits of phosphates and also the anti-bacterial and anti-biofilm benefits of a cationic antibacterial agent.

BRIEF SUMMARY

It is surprisingly found that addition of a stabilizing amount of an anionic surfactant, e.g. sodium lauryl sulfate, to formulations comprising a short chain polyphosphate salt and a cationic antibacterial agent inhibits the association of these components and enhances delivery to the teeth.

For example, quaternary ammonium antimicrobial agents such as cetyl pyridinium chloride (CPC) are generally incompatible with anionic polyphosphate salts because of the resulting precipitation of both components. However, we have found that the addition of an anionic surfactant, such as sodium lauryl sulfate, provides needed stability and competition between the phosphates, the sulfate group of the surfactant, and the CPC—the result is to free CPC and make it more available for interaction with bacteria. In some embodiments, the addition of a nonionic surfactant, such as a poloxamer, e.g., poloxamer 407, further improves CPC availability through additional competition pathways between water, the sulfate group of the anionic surfactant, and the CPC. Without the anionic surfactant (and optionally the nonionic surfactant), a formulation with CPC and phosphate salts may have little better efficacy than a non-CPC containing material, or the media control.

Similarly, bisguanide antimicrobial agents such as chlorhexidine will generally complex with anionic polyphosphate salts no matter what steps are taken, given their high charge density and entropically driven precipitation reaction. Chlorhexidine will also react with anionic surfactants such as sodium lauryl sulfate and thus is often considered incompatible with SLS. See, e.g. Barkvoll, et al., "Interaction between chlorhexidine digluconate and sodium lauryl sulfate in vivo," J Clin Periodontol. (1989) 16(9):593-5.

But we have found that chlorhexidine and short chain polyphosphate salts can be formulated in such a way to prevent precipitation (or to re-dissolve the precipitate) through the inclusion of low levels of anionic surfactant, such as sodium lauryl sulfate (SLS). Additional surfactant, particularly nonionic surfactant, e.g., poloxamers, can be used in addition to the anionic surfactant and help solubilize the components of the formulation.

The cationic antimicrobial agents which can be stabilized in formulation with short chain linear polyphosphates and anionic surfactant may alternatively be selected from, or may further comprise, for example antimicrobial guanidinium polymers, e.g., as disclosed in WO 2010134904 A1, the contents of which are incorporated by reference herein, e.g., polymers or co-polymers of allylguanidine compounds and salts thereof; as well as cationic amino acids and/or metal cations.

The disclosure thus provides, in one embodiment, oral care compositions comprising:
(i) a short chain linear polyphosphate salt, for example a phosphate salt comprising a pyrophosphate or triphosphate anion and an alkali metal cation (e.g., potassium or sodium), for example selected from sodium tripolyphosphate, potassium tripolyphosphate, tetrasodium pyrophosphate, tetrapotassium pyrophosphate, and mixtures thereof;
(ii) an effective amount of orally acceptable cationic active agent, in free or orally acceptable salt form, e.g., selected from one or more of quaternary ammonium surfactants (such as cetyl pyridinium chloride (CPC)); bisguanides (e.g., orally acceptable salts of chlorhexidine, such as chlorhexidine digluconate, or of poly (hexamethylene biguanide), e.g., polihexanide); cationic amino acids (such as arginine, in free or salt form); antimicrobial guanidinium polymers; metal cations (such as zinc, calcium, or stannous ions; e.g., wherein the cation source is a metal salt or oxide, e.g., comprises stannous chloride, stannous fluoride, zinc citrate, zinc lactate, zinc phosphate, zinc oxide, or combinations thereof), or combinations thereof;
(iii) a stabilizing amount of an anionic surfactant, such as sodium, potassium, ammonium, and ethanolammonium salts of linear $C_8$-$C_{18}$ alkyl sulfates or $C_8$-$C_{18}$ alkyl ether sulfates, e.g., sodium laureth sulfate, sodium lauryl sulfate, ammonium lauryl sulfate; and
(iv) optionally an orally acceptable nonionic surfactant, for example selected from poloxamers, polyoxyethylenes and combinations thereof; and
(v) water.

The disclosure further provides methods of inhibiting dental erosion, staining, and/or biofilm formation comprising administering to the oral cavity a composition as described.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As is usual in the art, the compositions described herein are sometimes described in terms of their ingredients, notwithstanding that the ingredients may disassociate, associate or react in the formulation. Ions, for example, are commonly provided to a formulation in the form of a salt, which may dissolve and disassociate in aqueous solution. It is understood that the invention encompasses both the mixture of described ingredients and the product thus obtained.

In a first embodiment, the disclosure provides oral care compositions (Composition 1) comprising:
(i) a short chain polyphosphate salt;
(ii) an effective amount of orally acceptable cationic active agent, in free or orally acceptable salt form;
(iii) a stabilizing amount of an anionic surfactant; and
(iv) water.

For example, the disclosure provides embodiments of Composition 1 as follows:
1.1 Composition 1 wherein the short chain polyphosphate salt comprises a phosphate chain of three phosphates or less and a monovalent cation.
1.2 Any foregoing composition wherein the short chain polyphosphate salt comprises a pyrophosphate or triphosphate anion and an alkali metal cation, e.g., selected from sodium, potassium and combinations thereof.
1.3 Any foregoing composition wherein the short chain polyphosphate salt comprises sodium tripolyphosphate, tetrasodium pyrophosphate, tetrapotassium pyrophosphate or combinations thereof.
1.4 Any foregoing composition wherein the short chain polyphosphate salt comprises sodium tripolyphosphate.
1.5 Any foregoing composition wherein the short chain polyphosphate salt is present in an amount of 0.01 wt. % to 5.0 wt. %, 0.1 wt. % to 5.0 wt. %, 0.1 wt. % to 3 wt. %, 0.5 wt. % to 1.5 wt. %, or 1.0 wt. % based on the total weight of the composition.
1.6 Any foregoing composition wherein the orally acceptable cationic active agent is selected from one or more of quaternary ammonium surfactants (such as cetyl pyridinium chloride (CPC), bisguanides (such as chlorhexidine digluconate), cationic amino acids (such as arginine), metal cations (such as zinc, calcium, or stannous ions), guanidinium polymers, or combinations thereof.
1.7 Any foregoing composition wherein the orally acceptable cationic active agent is selected from one or more of quaternary ammonium surfactants (such as cetyl pyridinium chloride (CPC)); bisguanides (e.g., orally acceptable salts of chlorhexidine, e.g., chlorhexidine digluconate, or poly(hexamethylene biguanide), e.g., polihexanide; cationic amino acids (such as arginine, in free or salt form); antimicrobial guanidinium polymers; metal cations (such as zinc, calcium, or stannous ions; e.g., wherein the cation source is a metal salt or oxide, e.g., comprises stannous chloride, stannous fluoride, zinc citrate, zinc lactate, zinc phosphate, zinc oxide, or combinations thereof), or combinations thereof.
1.8 Any foregoing composition wherein the orally acceptable cationic active agent is selected from one or more of quaternary ammonium surfactants (such as cetyl pyridinium chloride (CPC)) and bisguanides (e.g., orally acceptable salts of chlorhexidine, e.g., chlorhexidine digluconate, or poly(hexamethylene biguanide), e.g., polihexanide.

1.9 Any foregoing composition wherein the orally acceptable cationic active agent comprises a pyridinium surfactant, e.g., cetyl pyridinium chloride (CPC).

1.10 Any foregoing composition wherein the orally acceptable cationic active agent comprises chlorhexidine, in free base or orally acceptable salt form, e.g., chlorhexidine digluconate.

1.11 Any foregoing composition wherein the orally acceptable cationic active agent comprises arginine.

1.12 Any foregoing composition wherein the orally acceptable cationic active agent comprises zinc ions.

1.13 Any foregoing composition wherein the orally acceptable cationic active agent is provided by an orally acceptable salt selected from zinc salts, stannous salts, pyridinium salts, and bisguanide salts.

1.14 Any foregoing composition wherein the orally acceptable cationic active agent comprises metal ions supplied by one or more of stannous chloride, stannous fluoride, zinc citrate, zinc lactate, zinc phosphate, and zinc oxide.

1.15 Any foregoing composition wherein the orally acceptable cationic active agent is provided by an orally acceptable salt selected from cetyl pyridinium chloride and chlorhexidine digluconate.

1.16 Any foregoing composition wherein the orally acceptable cationic active agent is provided by an orally acceptable zinc salt, stannous salt or combination thereof.

1.17 Any foregoing composition wherein the effective amount of cationic active agent, in free or salt form, is present and comprises cetyl pyridinium chloride, in an amount of 0.05 to 0.1%, e.g., about 0.075%.

1.18 Any foregoing composition wherein the effective amount of cationic active agent, in free or salt form, is present and comprises chlorhexidine digluconate, in an amount of 0.1 to 0.2%, e.g., about 0.12%.

1.19 Any foregoing composition wherein the anionic surfactant comprises an alkyl sulfate or an alkyl ether sulfate in free or orally acceptable salt form.

1.20 Any foregoing composition wherein the anionic surfactant comprises a sodium, potassium, ammonium, and ethanolammonium salts of linear C8-C18 alkyl sulfate or C8-C18 alkyl ether sulfate.

1.21 Any foregoing composition wherein the anionic surfactant comprises sodium laurel ether sulfate (SLES), sodium lauryl sulfate, and ammonium lauryl sulfate.

1.22 Any foregoing composition wherein the anionic surfactant comprises sodium laurel sulfate.

1.23 Any foregoing composition wherein the anionic surfactant is present in an amount sufficient to substantially interfere with interaction between a cationic active agent and the short chain polyphosphate salt, e.g. an amount sufficient to inhibit formation of a precipitate or reduction of the efficacy of the cationic active agent.

1.24 Any foregoing composition wherein the anionic surfactant is present in an amount of 0.01 to 5.0%, 0.1 to 2.0%, 0.1 to 1.0%, 0.2 to 0.4%, or about 0.33%.

1.25 Any foregoing composition further comprising a nonionic surfactant.

1.26 Any foregoing composition comprising a nonionic surfactant selected from poloxamers or polyoxyethylene, poloxamer 407.

1.27 Any foregoing composition comprising a nonionic surfactant which is a block copolymer of polyethylene glycol and polypropylene glycol.

1.28 Any foregoing composition comprising a nonionic surfactant in an amount of about 0.01 to 5.0%, 0.1 to 2.0%, 0.1 to 0.6%, 0.2 to 0.4%, about 0.2%, or about 0.5%.

1.29 Any foregoing composition comprising a nonionic surfactant wherein the ratio of anionic surfactant to nonionic surfactant is about 5:1 to about 1:5; about 2:1 to about 1:2; about 1.5:1 to about 1:1.5; about 1.6:1; or about 1:1.5.

1.30 Any foregoing composition further comprising an amino acid or a polyamine, in free or orally acceptable salt form.

1.31 Any foregoing composition comprising a polyamine, in free or orally acceptable salt form, selected from lysine or arginine, in free or orally acceptable salt form.

1.32 Any foregoing composition wherein the composition comprises 0.01%-5% lysine, e.g., 0.5%-1.0% lysine, in free or orally acceptable salt form.

1.33 Any foregoing composition wherein the composition comprises 0.01%-5% arginine, e.g., 0.4%-0.8% arginine, in free or orally acceptable salt form.

1.34 Any foregoing composition wherein the composition comprises lysine in the form of a hydrochloride salt.

1.35 Any foregoing composition wherein the composition comprises 0.01%-2.0% lysine hydrochloride.

1.36 Any foregoing composition wherein the composition comprises greater than 50% water.

1.37 Any foregoing composition wherein the composition comprises 70% to 95% water.

1.38 Any foregoing composition wherein the composition comprises one or more of a thickener, a buffer, a humectant, a surfactant, an abrasive, a sweetener, a flavorant, a pigment, a dye, an anti-caries agent, an anti-bacterial agent, a whitening agent, a desensitizing agent, a preservative, or a mixture thereof.

1.39 Any foregoing composition wherein the composition comprises a phosphate buffer.

1.40 Any foregoing composition wherein the composition comprises a buffer wherein the buffer comprises sodium hydroxide.

1.41 Any foregoing composition further comprising a pH adjustment agent selected from lactic acid, citric acid, hydrochloric acid, glycolic acid, sodium hydroxide, potassium chloride, monosodium citrate, disodium citrate, monosodium malate, sodium carbonate, bicarbonates, sesquicarbonates, borates, silicates, monosodium phosphate, trisodium phosphate, pyrophosphate salts, imidazole, or combinations thereof, e.g., citric acid.

1.42 Any foregoing composition comprising a pH adjustment agent in an amount of 0.01% to 5.0%, 0.01% to 2.0%, 0.1% to 1.0%, or about 0.5%.

1.43 Any foregoing composition wherein the composition has a pH of about 1 to 7, about 3 to 6, about 5 to 6, or about 5.25 to 5.75.

1.44 Any foregoing composition wherein the composition comprises a humectant, e.g. selected from sorbitol, propylene glycol, glycerin, and combinations thereof 1.45 Any foregoing composition wherein the composition comprises a humectant, wherein the humectant is a mixture of glycerin, sorbitol, and propylene glycol.

1.46 Any foregoing composition wherein the composition comprises an abrasive.
1.47 Any foregoing composition wherein the composition comprises an abrasive, wherein the abrasive comprises silica.
1.48 Any foregoing composition wherein the composition a sweetener.
1.49 Any foregoing composition wherein the composition a sweetener, wherein the sweetener is sodium saccharin.
1.50 Any foregoing composition wherein the composition comprises a flavorant.
1.51 Any foregoing composition wherein the composition comprises a dye, e.g., FD&C Blue No. 1.
1.52 Any foregoing composition wherein the composition comprises an anti-caries agent.
1.53 Any foregoing composition wherein the composition comprises a fluoride ion source.
1.54 Any foregoing composition wherein the composition comprises a fluoride ion source, wherein the fluoride ion source is stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, or a mixture thereof.
1.55 Any foregoing composition wherein the composition comprises a whitening agent.
1.56 Any foregoing composition wherein the composition comprises a whitening agent, wherein the whitening agent is hydrogen peroxide.
1.57 Any foregoing composition wherein the composition comprises a desensitizing agent, a vitamin, a preservative, an enzyme, or a mixture thereof.
1.58 Any foregoing composition wherein the composition is a mouthwash, toothpaste, tooth gel, tooth powder, non-abrasive gel, mousse, foam, mouth spray, lozenge, oral tablet, dental implement, or pet care product.
1.59 Any foregoing composition wherein the composition is a mouthwash.
1.60 Any foregoing composition which is biphasic, e.g., wherein the solution comprises two distinct aqueous phases having different composition and density.
1.61 Any foregoing composition which comprises less than 5%, e.g., less than 2% of hydrophobic ingredients.
1.62 Any foregoing composition which is essentially oil-free, apart from flavoring agents.
1.63 Any foregoing composition wherein there is no visible precipitation or reaction between the short chain polyphosphate salt and the orally acceptable cationic active agent after three months of storage at room temperature.
1.64 Any foregoing composition for use in any of Methods A-E.
1.65 Any foregoing composition obtained or obtainable by Method F, infra.
1.66 Any foregoing composition wherein the composition is a mouthwash, wherein
  (i) the short chain polyphosphate salt comprises sodium tripolyphosphate in an amount of about 0.1 to 5%, e.g., 0.5-3%, e.g., 1-2%;
  (ii) the effective amount of orally acceptable cationic active agent, in free or orally acceptable salt form, comprises chlorhexidine in an amount of 0.1 to 0.2%;
  (iii) the anionic surfactant comprises sodium lauryl sulfate in an amount of 0.1 to 2.0%; and
  (iv) the amount of water is 70-95%, e.g. 75-85%;
  wherein the composition further comprises a poloxamer, e.g., poloxamer 407, poloxamer 335 or combinations thereof, e.g. poloxamer 407, in an amount of 0.05-1%, e.g., 0.1-0.3%;
  wherein the composition further comprises humectant comprising sorbitol, propylene glycol, glycerin, or combinations thereof, in an amount of 10-30%, e.g. 15-25%; and
  wherein all amounts are by weight of the total composition.

Further claimed is the use of an anionic surfactant, in free or orally acceptable salt form, to stabilize an oral care formulation comprising a short chain polyphosphate salt and an effective amount of orally acceptable cationic active agent, in free or orally acceptable salt form; for example, use in any of the foregoing Compositions 1, et seq.

As used herein, an "oral care composition" refers to a composition for which the intended use can include oral care, oral hygiene, or oral appearance, or for which the intended method of use can comprise administration to the oral cavity. The term "oral care composition" thus specifically excludes compositions which are highly toxic, unpalatable, or otherwise unsuitable for administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans. Oral care compositions include, for example, dentifrice and mouthwash. In some embodiments, the disclosure provides mouthwash formulations.

As used herein, "orally acceptable" refers to a material that is safe and palatable at the relevant concentrations for use in an oral care formulation, such as a mouthwash or dentifrice.

As used herein, "orally acceptable carrier" refers to any vehicle useful in formulating the oral care compositions disclosed herein. The orally acceptable carrier is not harmful to a mammal in amounts disclosed herein when retained in the mouth, without swallowing, for a period sufficient to permit effective contact with a dental surface as required herein. In general, the orally acceptable carrier is not harmful even if unintentionally swallowed. Suitable orally acceptable carriers include, for example, one or more of the following: water, a thickener, a buffer, a humectant, a surfactant, an abrasive, a sweetener, a flavorant, a pigment, a dye, an anti-caries agent, an anti-bacterial, a whitening agent, a desensitizing agent, a vitamin, a preservative, an enzyme, and mixtures thereof.

As used herein, "short chain polyphosphate salt" encompasses orally acceptable mono- and polyphosphates, for example, $P_{1-6}$ phosphates such as monobasic, dibasic or tribasic orthophosphate; and dimeric phosphates, e.g., sodium hexametaphosphate. For example, the short chain polyphosphate salt may comprise alkali dibasic orthophosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$). In one embodiment, tetrasodium pyrophosphate (TSPP), sodium tripolyphosphate (STPP), tetrapotassium pyrophosphate (TKPP), or mixtures thereof are used. In another embodiment, the compositions comprise a mixture of tetrapotassium pyrophosphate (TSPP) and sodium tripolyphosphate (STPP) ($Na_5P_3O_{10}$). Such phosphates are provided in an amount effective to reduce stains on tooth surfaces, erosion of the enamel, to aid in cleaning the teeth, and/or reduce tartar buildup on the teeth, for example, in an amount of 0.01 wt. % to 5.0 wt. %, 0.1 wt. % to 5.0 wt. %, 0.1 wt. % to 3 wt. %, 0.5 wt. % to 1.5 wt. %, or 1.0 wt. % based on the total weight of the composition.

As used herein, "orally acceptable cationic active agent" means an agent which is cationic in aqueous solution at neutral pH and which provides some benefit, e.g. antimicrobial, antigingivitis, and/or antierosion activity, to the teeth or oral cavity. While in aqueous formulation, the agent will generally be in solution, but it may be introduced to the formulation formulated in free or orally acceptable salt form. In certain embodiments, the orally acceptable cationic active agent is selected from one or more of quaternary ammonium surfactants (such as cetyl pyridinium chloride (CPC)), bisguanides (such as chlorhexidine digluconate), cationic amino acids (such as arginine), metal cations (such as zinc, calcium, or stannous ions), or combinations thereof.

As used herein, "anionic surfactant" means those surface-active or detergent compounds that contain an organic hydrophobic group containing generally 8 to 26 carbon atoms or generally 10 to 18 carbon atoms in their molecular structure and at least one water-solubilizing group selected from sulfonate, sulfate, and carboxylate so as to form a water-soluble detergent. Usually, the hydrophobic group will comprise a $C_8$-$C_{22}$ alkyl, or acyl group. Such surfactants are employed in the form of water-soluble salts and the salt-forming cation usually is selected from sodium, potassium, ammonium, magnesium and mono-, di- or tri-$C_2$-$C_3$ alkanolammonium, with the sodium, magnesium and ammonium cations again being the usual ones chosen. Some examples of suitable anionic surfactants include, but are not limited to, the sodium, potassium, ammonium, and ethanolammonium salts of linear $C_8$-$C_{18}$ alkyl ether sulfates, ether sulfates, and salts thereof. Suitable anionic ether sulfates have the formula $R(OC_2H_4)_n OSO_3M$ wherein n is 1 to 12, or 1 to 5, and R is an alkyl, alkylaryl, acyl, or alkenyl group having 8 to 18 carbon atoms, for example, an alkyl group of $C_{12}$-$C_{14}$ or $C_{12}$-$C_{16}$, and M is a solubilizing cation selected from sodium, potassium, ammonium, magnesium and mono-, di- and triethanol ammonium ions. Exemplary alkyl ether sulfates contain 12 to 15 carbon atoms in the alkyl groups thereof, e.g., sodium laureth (2 EO) sulfate. Some preferred exemplary anionic surfactants that may be used in the compositions of the present disclosure include sodium laurel ether sulfate (SLES), sodium lauryl sulfate, and ammonium lauryl sulfate. In certain embodiments, the anionic surfactant is present in an amount of 0.01 to 5.0%, 0.1 to 2.0%, 0.2 to 0.4%, or about 0.33%.

As used herein, "nonionic surfactant" generally refers to compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name PLURONIC®), polyoxyethylene, polyoxyethylene sorbitan esters (sold under trade name TWEENS®), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, alkyl polyglycosides (for example, fatty alcohol ethers of polyglycosides, such as fatty alcohol ethers of polyglucosides, e.g., decyl, lauryl, capryl, caprylyl, myristyl, stearyl and other ethers of glucose and polyglucoside polymers, including mixed ethers such as capryl/caprylyl ($C_{8-10}$) glucoside, coco ($C_{8-16}$) glucoside, and lauryl ($C_{12-16}$) glucoside), long chain tertiary amine oxides, long chain tertiary phosphine oxides, long chain dialkyl sulfoxides, and mixtures of such materials.

In some embodiments, the nonionic surfactant comprises amine oxides, fatty acid amides, ethoxylated fatty alcohols, block copolymers of polyethylene glycol and polypropylene glycol, glycerol alkyl esters, polyoxyethytene glycol octylphenol ethers, sorbitan alkyl esters, polyoxyethylene glycol sorbitan alkyl esters, and mixtures thereof. Examples of amine oxides include, but are not limited to, laurylamidopropyl dimethylamine oxide, myristylamidopropyl dimethylamine oxide, and mixtures thereof. Examples of fatty acid amides include, but are not limited to, cocomonoethanolamide, lauramide monoethanolamide, cocodiethanolamide, and mixtures thereof. In certain embodiments, the nonionic surfactant is a combination of an amine oxide and a fatty acid amide. In certain embodiments, the amine oxide is a mixture of laurylamidopropyl dimethylamine oxide and myristylamidopropyl dimethylamine oxide. In certain embodiments, the nonionic surfactant is a combination of lauryl/myristylamidopropyl dimethylamine oxide and cocomonoethanolamide. In certain embodiments, the nonionic surfactant is present in an amount of 0.01 to 5.0%, 0.1 to 2.0%, 0.1 to 0.6%, 0.2 to 0.4%, about 0.2%, or about 0.5%.

As used herein "polyamine compound" means a molecule having at least two primary or secondary amine groups, for example having an isoelectric point of greater than pH 8.5, for example pH 9-10. Examples of polyamines include ethylene diamine, lysine, or histadine, as well as polymers such as Lupasol P, which is a polyethylenimine. The polyamine must be safe for its intended use. Where the composition is an oral care composition, the polyamine must be orally acceptable. The polyamine may be provided in free or acid addition salt form. In certain embodiments the polyamine compound is lysine.

As used herein, "biphasic" refers to stable liquid compositions which contain at least two distinct homogeneous phases, having different densities, such that the phases are separate at rest. The phases may be readily mixed by shaking but will then re-separate over a short period, e.g., less than half an hour. In certain embodiments, the term excludes gels, emulsions, microemulsions, and homogeneous solutions. In certain embodiments, these formulations differ from conventional biphasic formulations in that both phases are aqueous, rather than one phase being hydrophobic and the other hydrophilic.

As used herein, a "tartar control agent" refers to a compound or a mixture of compounds that inhibit the formation of tartar, a mixture of calcium phosphates on organic matrices, and/or the deposition of plaque on teeth to form tartar (calculus).

As used herein, "chemical stain" refers to a discoloration of a dental surface caused by adsorption or absorption of a colored agent on or into the surface, or caused by chemical reaction of material of the dental surface (e.g., dental enamel) with a colored or noncolored agent contacting the surface. "Chemical staining" herein means formation and/or development of a chemical stain.

As used herein, "dental surface" refers to a surface of a natural tooth or a hard surface of artificial dentition including a crown, cap, filling, bridge, dental implant and the like. In some embodiments, the dental surface is a natural tooth.

The compositions are, for example, oral care compositions, in accordance with Composition 1, et seq. for example mouthwashes. Any of the compositions of Composition 1, et seq. is suitable for oral care use, provided the ingredients are orally acceptable. In some embodiments, the mouthwash of Composition 1 comprises an effective amount of an orally acceptable cationic active agent, which is an antimicrobial, antigingivitis, anti-erosion and/or anti-caries agent, e.g. a cationic active agent selected from one or more of quaternary ammonium surfactants (such as cetyl pyridinium chloride (CPC)), bisguanides (such as chlorhexidine digluconate), cationic amino acids (such as arginine), metal cations (such as zinc, calcium, or stannous ions), or combinations thereof. The orally acceptable cationic active agent may be present in an effective amount, for example an antimicrobial, antigingivitis, anti-erosion and/or anti-caries amount. The precise amount will depend on the particular active agent and the condition to be treated or prevented, but in various embodiments, antimicrobially effective levels of CPC in a mouthwash would include amounts from 0.05 to 0.1%, e.g., about 0.075%; antimicrobially effective levels of chlorhexidine digluconate in a mouthwash would include amounts from 0.1-0.2%, e.g., about 0.12%; anti-erosion or antimicrobial levels of metal cations such as zinc (e.g., zinc citrate or other soluble salt) or stannous (e.g., stannous fluoride and/or stannous chloride) would be on the order of 100-1500 ppm.

The oral care composition used in the present disclosure comprise significant levels of water. Water employed in the preparation of commercial oral compositions should be deionized and free of organic impurities. The amount of water in the compositions includes the free water that is added plus that amount which is introduced with other materials.

Mouthwashes frequently contain significant levels of ethanol, which is often needed to solubilize essential oils and to prevent bacterial contamination. High levels of ethanol may be undesirable, because in addition to the potential for abuse by ingestion, the ethanol may exacerbate conditions like xerostoma. Accordingly, in some embodiments, the oral care compositions of the invention are substantially free of ethanol, e.g., contain less than 1% ethanol.

Humectants can enhance the viscosity, mouthfeel, and sweetness of the product, and may also help preserve the product from degradation or microbial contamination. Suitable humectants include edible polyhydric alcohols such as glycerin, sorbitol, xylitol, propylene glycol as well as other polyols and mixtures of these humectants. Sorbitol may in some cases be provided as a hydrogenated starch hydrolysate in syrup form, which comprises primarily sorbitol (the product if the starch were completely hydrolyzed to glucose, then hydrogenated), but due to incomplete hydrolysis and/or presence of saccharides other than glucose, may also include other sugar alcohols such mannitol, maltitol, and longer chain hydrogenated saccharides, and these other sugar alcohols also function as humectants in this case. In some embodiments, humectants are present at levels of 5% to 30%, e.g., 10% to 20% by weight.

Flavorings for use in the present invention may include extracts or oils from flavorful plants such as peppermint, spearmint, cinnamon, wintergreen, and combinations thereof, cooling agents such as menthol, methyl salicylate, and commercially available products such as OptaCool® from Symrise, as well as sweeteners, which may include polyols (which also function as humectants), saccharin, acesulfame, aspartame, neotame, stevia and sucralose.

Further provided is a method (Method A) for the treatment and/or inhibition of a chemical stain, plaque, and/or tartar on a dental surface, comprising contacting the dental surface with any of the preceding oral care compositions.

Further provided herein is Method A as follows:
A.1 Method A wherein the composition is Composition 1, e.g., selected from any of Compositions 1.1-1.63.
A.2 Method A or A.1 wherein the method is for the treatment of a chemical stain, plaque, and/or tartar on the dental surface.
A.3 Method A.2 wherein the method is for the treatment of a chemical stain on the dental surface.
A.4 Method A.2 wherein the method is for the treatment of plaque on the dental surface.
A.5 Method A.2 wherein the method is for the treatment of tartar on the dental surface.
A.6 Method A or A.1 wherein the method is for the inhibition of a chemical stain, plaque, and/or tartar on the dental surface.
A.7 Method A.6 wherein the method is for the inhibition of a chemical stain on the dental surface.
A.8 Method A.6 wherein the method is for the inhibition of plaque on the dental surface.
A.9 Method A.6 wherein the method is for the inhibition of tartar on the dental surface.
A.10 Method A or A.1-A.9 wherein the dental surface is a human tooth.
A.11 Method A or A.1-A.10 wherein the composition is contacted with the dental surface by brushing.
A.12 Any foregoing Method A, et seq. wherein e formulation is biphasic and is shaken before use.

Further provided is a method (Method B) for the treatment and/or inhibition of gum disease comprising contacting the oral cavity with any of the preceding oral care compositions.

Further provided herein is Method B as follows:
B.1 Method B wherein the composition is Composition 1, e.g., any of Compositions 1.1-1.63.
B.2 Method B or B.1 wherein the method is for the treatment of gum disease.
B.3 Method B, B.1, or B.2 wherein the gum disease is gingivitis.
B.4 Method B, B.1, or B wherein the gum disease is periodontitis.
B.5 Method B or B.1 wherein the method is for the inhibition of gum disease.
B.6 Method B, B.1, or B.5 wherein the gum disease is gingivitis.
B.7 Method B, B.1, or B.5 wherein the gum disease is periodontitis.
B.8 Method B or B.1-B.7 wherein the oral cavity is a human oral cavity.
B.9 Method B or B.1-B.8 wherein the composition is contacted with the oral cavity by brushing.
B.10 Any foregoing Method B, et seq. wherein the formulation is biphasic and is shaken before use.

Further provided is a method (Method C) for the treatment and/or inhibition of halitosis comprising contacting the oral cavity with any of the preceding oral care compositions.

Further provided herein is Method C as follows:
C.1 Method C wherein the composition is Composition 1, e.g., any of Compositions 1.1-1.63.
C.2 Method C or C.1 wherein the oral cavity is a human oral cavity.

C.3 Method C, C.1, or C.2 wherein the composition is contacted with the oral cavity by brushing.

C.4 Any foregoing Method C, et seq. wherein the formulation is biphasic and is shaken before use.

Further provided is a method (Method D) for inhibiting biofilm formation on a dental surface comprising contacting the dental surface with any of the preceding oral care compositions.

Further provided herein is Method D as follows:

D.1 Method D wherein the composition is Composition 1, e.g., any of Compositions 1.1-1.63.

D.2 Method D or D.1 wherein the dental surface is a human tooth.

D.3 Method D, D.1, or D.2 wherein the composition is contacted with the dental surface by brushing.

D.4 Any foregoing Method D, et seq. wherein the formulation is biphasic and is shaken before use.

Further provided is a method (Method E) for treating and/or inhibiting bacteria from aggregating and forming bigger colonies in an oral cavity comprising contacting the oral cavity with any of the preceding oral care compositions.

Further provided herein is Method E as follows:

E.1 Method E wherein the composition is Composition 1, e.g., any of Compositions 1.1-1.63.

E.2 Method E or E.1 wherein the oral cavity is a human oral cavity.

E.3 Method E, E.1, or E.2 wherein the composition is contacted with the oral cavity by brushing.

E.4 Any foregoing Method E, et seq. wherein the formulation is biphasic and is shaken before use.

Further provided are Compositions 1, et seq. for use in any of Methods A-E.

As used herein, "inhibition" refers to reduction of stains that would otherwise form or develop subsequent to the time of the treatment. Such inhibition can range from a small but observable or measurable reduction to complete inhibition of subsequent staining, by comparison with an untreated or placebo-treated dental surface.

Where the dental surface is substantially free of chemical stains, Method A, e.g., A.1-A.12, is effective to inhibit formation and development of new chemical stains, as can occur for example by oral use of tobacco products (including smoking) or by drinking tea, coffee, red wine, or cola beverages, subsequent to treatment according to the method. Where the dental surface already possesses some degree of chemical staining, Method A, e.g., A.1-A.12, is effective to inhibit further development of the existing stain. In some embodiments, the Method A, e.g., A.1-A.12, can remove, partially or completely, an existing chemical stain as well as inhibit subsequent staining.

We have further discovered that the formation of precipitating complexes between the phosphate and the cationic antibacterial is affected by the order in which the components are added. If the components are not added in the correct order, a precipitate is formed that will not redissolve. Thus, in another embodiment, the disclosure provides a method (Method F) of making an oral care composition comprising (i) a short chain polyphosphate salt [e.g., selected from tripolyphosphates, pyrophosphates and mixtures thereof, e.g. in sodium and/or potassium salt form, e.g., selected from sodium tripolyphosphate, potassium tripolyphosphate, tetrapotassium pyrophosphate, tetrasodium pyrophosphate, and mixtures of any two or more of these]; (ii) an effective amount of orally acceptable cationic active agent, in free or orally acceptable salt form [e.g. 0.1-1% of chlorhexidine or chlorhexidine digluconate]; (iii) a stabilizing amount of an anionic surfactant [e.g., 0.1-1% sodium lauryl sulfate]; (iv) water; and optionally one or more of a basic amino acid in free or salt form [e.g. 0.5-1% lysine or 0.4-0.8% arginine, e.g., as a solid], humectant, nonionic polymer, flavoring and/or dye (e.g., a method of making an oral care composition according to any of Compositions 1, et seq.); the method comprising the following steps in the following order:

a) adding the stabilizing amount of an anionic surfactant to water;

b) adding a dilute solution of the effective amount of orally acceptable cationic active agent, in free or orally acceptable salt form, [e.g., adding an aqueous solution having a concentration of 0.1% to 5%, e.g., 0.5% to 2%, e.g., about 1% of active] to the product of step a);

c) adding the short chain polyphosphate salt in solid form to the product of step b);

d) optionally admixing to the solution thus obtained one or more of a basic amino acid in free or salt form [e.g. 0.5-1% lysine or 0.4-0.8% arginine, e.g., as a solid], humectant, nonionic polymer, flavoring and/or dye;

wherein during addition steps a), b) and c), the pH is maintained between pH 5 and 6, e.g., between pH 5.25-5.75, e.g. using a pH adjusting agent, e.g. citric acid.

In another embodiment, the disclosure provides an oral care composition or oral composition premix, comprising (i) a short chain polyphosphate salt; (ii) an effective amount of orally acceptable cationic active agent, in free or orally acceptable salt form; (iii) a stabilizing amount of an anionic surfactant; and (iv) water (e.g., an oral care composition according to any of Compositions 1, et seq.) obtained or obtainable by the process of Method F.

EXAMPLES

Example 1—Chlorhexidine and Anti-Stain Polyphosphate Salts

Chlorhexidine (CHX) mouthwash is very effective to fight gingivitis. But after CHX has been adsorbed to a tooth surface, stains often result after drinking coffee, tea, or red wine, primarily occurring through charge interaction between the positively charged CHX and negatively charged stains. This means that someone using a chlorhexidine must either avoid foods and beverages with a dark color, or become accustomed to teeth that are more yellow and stained.

Sodium tripolyphosphate (STPP) exhibits significant stain fighting ability, and when used in oral care products, deposits onto a tooth surface. However, when STPP and CHX are combined, complexes formed by the two can result in precipitation of both STPP and CHX, inactivating both components.

We have found, however, that CHX and STPP can be formulated in such a way to prevent precipitation (or to re-dissolve the precipitate) through the inclusion of sodium lauryl sulfate. Additionally, the nonionic surfactant Poloxamer 407 can be used to supplement portions of SLS. The following formulations are tested:

TABLE 1

Test formulations

| Materials | Formulation 1 (wt. %) | Formulation 2 (wt. %) |
|---|---|---|
| Chlorhexidine digluconate (20% solution) | 0.6386 (0.1277 active) | 0.6386 (0.1277 active) |
| Poloxamer 407 (nonionic surfactant) | 0.2 | 0.2 |
| Sodium Tripolyphosphate | 1.0 | 1.0 |
| Sodium lauryl sulfate (anionic surfactant) | 0.325 | 0.325 |
| Glycerine | 7.2 | 7.2 |
| Sorbitol (70% solution) | 9.6 (6.7 active) | 9.6 (6.7 active) |
| Propylene Glycol | 7.0 | 7.0 |
| Flavor | 0.1 | 0.1 |
| FD&C Blue No. 1 | 0.0001 | 0.0001 |
| Citric Acid Monohydrate | 0.5 | 0.5 |
| Lysine hydrochloride | — | 1.0 |
| Water | q.s. | q.s. |

Method of Preparation:

Sodium lauryl sulfate is added as a solid to water, which results in a clear solution as the sodium lauryl sulfate dissolves. A 1% diluted solution of chlorhexidine is then added to the solution. The chlorhexidine is added dropwise over a period of about one minute. Sodium tripolyphosphate is then dissolved into the solution. The pH is maintained between 5.25-5.75 using a pH adjusting agent, such as citric acid. Poloxamer 407 may then be added to the solution to enhance solution clarity.

Stain Reduction:

The efficacy of the test formulations on staining is tested against a commercial 0.12% chlorhexidine digluconate (CHX) mouthwash. Table 2 below compares the change in color (ΔW) of hydroxyapatite (HAP) discs treated with various solutions. Each HAP disc is soaked in centrifuged saliva for at least two hours at 37° C. After this time, the discs are rinsed with water and then transferred to the solutions listed for 15 minutes at 37° C. This is repeated two more times for a total of three CHX treatments. The discs are rinsed a final time, then put in a coffee/tea/wine solution for 15 minutes with shaking at 37° C. The discs are removed and rinsed, and the change in color (ΔW) is measured.

The results are as follows:

TABLE 2

Stain protection with various formulations

| Compositions (wt. %) | Commercial 0.12% CHX | 0.12 CHX, 0.2 P407, 0.325 SLS | 0.12 CHX, 1 STPP, 0.2 P407, 0.325 SLS |
|---|---|---|---|
| ΔW | 35.3 | 24.5 | 14.9 |

CHX = chlorhexidine digluconate;
SLS = sodium lauryl sulfate (anionic surfactant);
P407 = poloxamer 407 (nonionic surfactant);
STPP = sodium tripolyphosphate.

As expected, the discs treated with commercial chlorhexidine mouthwash and red wine exhibit considerable staining. Combining CHX with the surfactant combination SLS and P407 consistently provides a degree of stain prevention. However, when STPP is included in the formulation, ΔW decreases by about 50%, which is a significant increase in stain preventing power.

Bacterial kill: A 20-second short interval kill test (SIKT) measures the efficacy of various treatment solutions in killing oral pathogens. The Fluorescent SIKT uses Live/Dead BacLight fluorescent viability staining system to measure permeabilization of bacteria by single actives or liquid formulations. A mixed species inoculum culture containing: *Lactobacillus casei, Streptococcus oralis, Actinomyces viscosus, Veillonella parvula & Fusobacterium nucleatum* at an optical density of 0.5 @ 610 nm is centrifuged. The supernatant is then aspirated off and the remaining pellicle is re-suspended in sterile phosphate buffered saline (PBS). 100 μl of this solution is then treated with 100 μl of test sample for 30 or 60 seconds. Immediately following treatment, the exposure is neutralized by adding 1.3 ml of sterile D/E neutralizing broth. The neutralizing broth is then rinsed off by centrifugation and re-suspension in PBS. 50 μl samples are then transferred in triplicate to a 96-well microplate. The fluorescent dyes are then prepared per the manufacturer's directions and added to the samples. The fluorescence is then measured in a fluorescent plate reader. Data from this assay are presented as a percentage of bacterial remaining viable relative to a control sample treated with PBS. The formulations containing Poloxamer 407 and STPP provided a reduction of about 70% reduction in bacterial viability vs. about 50% for a commercial formulation lacking these ingredients. The percent viability of different formulations, wherein lower percent viability corresponds higher bacteriocidal activity, is set forth in table 3.

TABLE 3

SIKT with different formulations

| Compositions (wt. %) | Commercial 0.12% CHX | 1.0 STPP, 0.2 P407, 0.325 SLS, 0.12 CHX | 1.0 STPP, 0.5 P407, 0.325 SLS, 0.12 CHX |
|---|---|---|---|
| % viability | 50.5 | 29.6 | 32.9 |

Stain Deposition:

Saliva-coated hydroxyapatite (HAP) disks are treated with either the commercial CHX mouthwash formulation or Formulation 1, as used in Example 1, and the disks are then challenged with a staining solution containing a coffee, tea and wine mixture. Briefly, HAP disks are incubated in 1 mL of saliva in a shaker bath, 37° C., overnight. After rinsing with distilled water, baseline spectrophotometer measurements are taken. 2 mL of the test formulation is added and the disk is incubated in the shaker bath at 37° C. for 30 seconds. After rinsing with distilled water, spectrophotometer measurements are repeated. 2 mL of the stain solution is then added, and the disks are incubated in the shaker bath at 37° C. for 15 min. After rinsing with distilled water, spectrophotometer measurements are taken again. This treatment/stain procedure is repeated for a total of three staining cycles. The spectrophotometer measurements are used to evaluate change in color values (abL). Stain prevention efficacy is measured as ΔE (Et−Ei) and/or ΔW* (W*t−W*i) according to known methods. The results are shown in Table 4 below. The results demonstrate that Formulation 1 is significantly more effective in preventing stain deposition than the commercial CHX formulation.

TABLE 4

| Stain Cycle | Commercial CHX (ΔW) | Formulation 1 (ΔW) |
|---|---|---|
| First | 17.4 | 7.7 |
| Second | 24.6 | 15.2 |
| Third | 29.5 | 21.0 |

Bacterial Kill Efficacy:

A five-day biofilm assay is performed to compare the efficacy of Formulation 1 with and without chlorhexidine in the presence of sodium lauryl sulfate. The active attachment biofilm model (Extrecate et al., Caries Research 2010; 44:372-379) is used to measure the antibacterial efficacy of the mouthwash formulations. In this model, 24 hydroxyapatite (HAP) discs are clamped onto a sterile metal lid. The lid is then inoculated in 2% unstimulated saliva in McBain medium for 24 hours at 37° C. on a 24-well plate under anaerobic conditions. After initial attachment, the biofilms are transferred into fresh growth media for maturation. Treatment is performed after formation of a 24 hour biofilm. The HAP discs are treated for 10 minutes at room temperature in 1.6 ml of the mouthwash formulation. The lid is subsequently transferred to a new plate for washing with 1.7 ml 25% Tryptic Soy Buffer and moved up and down 10 times. The wash step is repeated three times. The biofilms are then transferred into McBain medium and incubated anaerobically at 37° C. The discs are treated seven times over a 5-day period and the resulting biofilms are harvested using sonication. The harvested biofilms are subjected to ATP metabolic assay (Life Technology) and plated on 5% sheep blood agar plate to determine total colony counts. The results are reported as log(CFU/ml) for four replicates of each sample. The results are shown in Table 5 below. These results demonstrate that the chlorhexidine present in Formulation 1 is effective at killing bacteria despite the presence of sodium lauryl sulfate.

TABLE 5

| Formula | Log CFU/mL |
| --- | --- |
| Untreated control | 9.59 |
| Formulation 1 without CHX | 8.02 |
| Formulation 1 | 6.06 |

The invention claimed is:

1. An oral care composition comprising
   a) a short chain polyphosphate salt;
   b) an effective amount of orally acceptable cationic active agent, in free or orally acceptable salt form, wherein the orally acceptable cationic active agent is cetyl pyridinium chloride;
   c) a stabilizing amount of an anionic surfactant; and
   d) water.

2. The composition of claim 1 wherein the short chain polyphosphate salt comprises a pyrophosphate or triphosphate anion and an alkali metal cation.

3. The composition of claim 1 wherein the short chain polyphosphate salt comprises sodium tripolyphosphate or tetrapotassium pyrophosphate.

4. The composition of claim 1 wherein the short chain polyphosphate salt comprises sodium tripolyphosphate, at a concentration of 0.1 wt. %-5.0 wt. %.

5. The composition of claim 1 wherein the orally acceptable cationic active agent is cetyl pyridinium chloride, at a concentration of 0.05 wt. %-1 wt. %.

6. The composition of claim 1 wherein the anionic surfactant comprises sodium laureth sulfate, sodium lauryl sulfate, ammonium lauryl sulfate, or combinations thereof.

7. The composition of claim 1 wherein the anionic surfactant comprises sodium lauryl sulfate, at a concentration of 0.1 wt. %-1.0 wt. %.

8. The composition of claim 1 further comprising a nonionic surfactant.

9. The composition of claim 1 wherein the composition comprises 70% to 95% water.

10. The composition of claim 1 wherein the composition comprises one or more of a thickener, a buffer, a humectant, a surfactant, an abrasive, a sweetener, a flavorant, a pigment, a dye, an anti-caries agent, an anti-bacterial agent, a whitening agent, a desensitizing agent, a preservative, or a mixture thereof.

11. The composition of claim 1 wherein the composition is a mouthwash.

12. The composition of claim 11 which is biphasic, wherein the solution comprises two distinct aqueous phases having different composition and density.

13. The composition of claim 1 wherein there is no visible precipitation or reaction between the short chain polyphosphate salt and the orally acceptable cationic active agent after three months of storage at room temperature.

14. A method for
   a) the treatment and/or inhibition of a chemical stain, plaque, and/or tartar on a dental surface,
   b) the treatment and/or inhibition of gum disease,
   c) the treatment and/or inhibition of halitosis,
   d) inhibiting biofilm formation on a dental surface, and/or
   e) treating and/or inhibiting bacteria from aggregating and forming bigger colonies in an oral cavity
   comprising contacting a dental surface with a composition according claim 1.

15. A method of making an oral care composition comprising (i) a short chain polyphosphate salt; (ii) an effective amount of orally acceptable cationic active agent, wherein the orally acceptable cationic active agent is cetyl pyridinium chloride, in free or orally acceptable salt form; (iii) a stabilizing amount of an anionic surfactant; (iv) water; and optionally, one or more of a basic amino acid in free or salt form, humectant, nonionic polymer, flavoring and/or dye, wherein the method comprises the following steps in the following order:
   a) adding the stabilizing amount of an anionic surfactant to the water;
   b) adding a dilute solution of the effective amount of orally acceptable cationic active agent, in free or orally acceptable salt form, to the product of step a);
   c) adding the short chain polyphosphate salt in solid form to the product of step b);
   d) optionally admixing to the solution thus obtained, one or more of a basic amino acid in free or salt form, humectant, nonionic polymer, flavoring and/or dye;
   wherein during addition steps a), b) and c), the pH is maintained between pH 5 and pH 6.

16. An oral care composition which is obtained or obtainable by the method of claim 15.

17. The composition of claim 1, wherein the short chain polyphosphate salt comprises sodium tripolyphosphate at a concentration of 0.1 wt. %-5.0 wt. %, cetyl pyridinium chloride is at a concentration of 0.05 wt. %-1 wt. %, and the anionic surfactant comprises sodium lauryl sulfate at a concentration of 0.1 wt. %-1.0 wt. %.

* * * * *

UNITED STATES PATENT AND TRADEMARK OFFICE
CERTIFICATE OF CORRECTION

PATENT NO. : 10,857,395 B2
APPLICATION NO. : 16/702618
DATED : December 8, 2020
INVENTOR(S) : Carl Myers et al.

Page 1 of 1

It is certified that error appears in the above-identified patent and that said Letters Patent is hereby corrected as shown below:

In the Specification

In Column 5, Line 55, delete "laurel" and insert -- lauryl --, therefor.

In Column 6, Line 3, before "poloxamer 407.", insert -- e.g., --.

In Column 12, Line 33, delete "e" and insert -- the --, therefor.

Signed and Sealed this
Ninth Day of March, 2021

Drew Hirshfeld
*Performing the Functions and Duties of the
Under Secretary of Commerce for Intellectual Property and
Director of the United States Patent and Trademark Office*